United States Patent [19]

Marazza et al.

[11] Patent Number: 5,239,074
[45] Date of Patent: Aug. 24, 1993

[54] DIASTEREOISOMERIC COMPOUNDS DERIVED FROM TETRAHYDROFOLIC ACID, PROCESS FOR THEIR PREPARATION AND USE IN THE SYNTHESIS OF DIASTEREOISOMERS 6S AND 6R OF REDUCED FOLATES

[75] Inventors: Fabrizio Marazza, Sorengo; Attilio Melera, Montagnola, both of Switzerland; René Viterbo, Paris, France

[73] Assignee: Sapec S.A., Switzerland

[21] Appl. No.: 784,422

[22] PCT Filed: Mar. 8, 1991

[86] PCT No.: PCT/FR91/00185

§ 371 Date: Nov. 6, 1991

§ 102(e) Date: Nov. 6, 1991

[87] PCT Pub. No.: WO91/13890

PCT Pub. Date: Sep. 19, 1991

[30] Foreign Application Priority Data

Mar. 9, 1990 [FR] France .................. 90 03032

[51] Int. Cl.$^5$ .................. C07D 498/22; C07D 487/14; C07D 475/04; A61K 31/505
[52] U.S. Cl. .................. 544/247; 544/251; 544/257
[58] Field of Search .................. 544/247; 548/237

[56] References Cited

U.S. PATENT DOCUMENTS 5,006,655  4/1991  Muller et al. .................. 544/258

FOREIGN PATENT DOCUMENTS 0266042  5/1988  European Pat. Off. .
0348641  1/1990  European Pat. Off. .
0409125  1/1991  European Pat. Off. .
2054597  2/1981  United Kingdom .

OTHER PUBLICATIONS

L. Rees, et al., "A simple and effective method for preparation of the 6(R)- and 6(S)-diasteroisomers of 5-formyltetrahydrofolate (Leucovorin)", *Journal of the Chemical Society*, Chemical Communications, 1987, pp. 470-472.

S. B. Horowitz, et all, "Diastereoisomers of formaldehyde derivatives of tetrahydrofolic acid and tetrahydroaminopterin", *Journal of Medicinal Chemistry*, vol. 12, No. 1, Jan. 1969, pp. 49-51.

C. Temple, Jr., et al., "Preparation and purification of L-(+)-5-formyl-5,6,7,8-tetrahydrofolic acid", *Journal of Medicinal Chemistry*, vol. 22, No. 6, Jun. 1979.

D. B. Cosulich, et al., "Diastereoisomers of Leucovorin", *Journal of the American Chemical Society*, vol. 74, No. 16, Aug. 20, 1952.

M. May et al., *J. Am. Chem. Soc.*, 73, 3067-3075, (1951).

J. C. Fontecilla-Camps et al., *J. Am. Chem. Soc.*, 101, 6114-6115, (1979) (see p. 4, lines 25-26).

J. C. Fontecilla-Camps et al., "Deveopments in Biochemistry", vol. 4, pp. 235-240, (1979).

R. Kalbermatten et al., *Helv. Chim. Acta*, 64, 2627-2635 (1981).

C. M. Tatum et al., *Biochemistry*, 16, 1093-1102, (1977).

*Primary Examiner*—Emily Bernhardt
*Attorney, Agent, or Firm*—Ostrolenk, Faber, Gerb & Soffen

[57] ABSTRACT

The present invention relates to a novel method of preparing diastereoisomers derived from tetrahydrofolic acid. By reacting (i) (6RS)-folinic acid or one of its salts, or (ii) 5,10-methenyl-5,6,7,8-tetrahydrofolic acid, with HCOOH at pH 2.0-2.6, a precipitate is obtained which consists of a mixture of two diastereoisomers of orthoamide structure and of the formulae

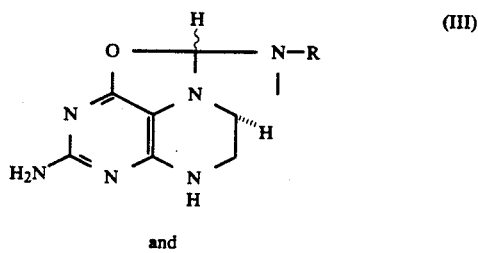

(III)

and (Abstract continued on next page).

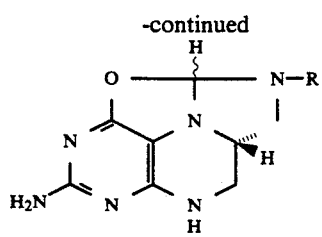

in which R is the p-benzoyl-(L)-glutamic acid residue, in a molar ratio IV/III of about 7/3, compound III being of so-called natural configuration and compound IV being of so-called unnatural configuration. The pure compound IV is isolated from said precipitate and the pure compound III is isolated from the corresponding filtrate. The diastereoisomers of the reduced folates and their salts of natural and unnatural configuration are prepared from compounds III and respectively IV.

11 Claims, No Drawings

DIASTEREOISOMERIC COMPOUNDS DERIVED FROM TETRAHYDROFOLIC ACID, PROCESS FOR THEIR PREPARATION AND USE IN THE SYNTHESIS OF DIASTEREOISOMERS 6S AND 6R OF REDUCED FOLATES

FIELD OF THE INVENTION

The present invention relates to a novel method of preparing diastereoisomeric compounds derived from tetrahydrofolic acid. These compounds include, by way of industrial products, (i) a mixture of the 6P and 6Q diastereoisomers as defined below (and probably having formulae III and respectively IV given below), in a molar ratio 6P/6Q of about 7/3, (ii) the pure 6P diastereoisomer and (iii) the pure 6Q diastereoisomer.

The invention further relates to the use of said 6P and 6Q diastereoisomers in the synthesis of the 6S and 6R diastereoisomers of reduced folates, such as the following acids in particular:
5-CHO-(6S)-THF,
5-CHO-(6R)-THF,
5-Me-(6S)-THF,
5-Me-(6R)-THF,
5,10-CH+-(6R)-THF and
5,10-CH+-(6S)-THF,
and their salts.

ABBREVIATIONS

For convenience, the following abbreviations have been used in the present description:
a) the reduced folates
THF = 5,6,7,8-tetrahydrofolic acid
5-CHO-(6RS)-THF = (6RS)-5-formyl-5,6,7,8-tetrahydrofolic acid (or (6RS)-folinic acid)
5-CHO-(6S)-THF = (6S)-5-formyl-5,6,7,8-tetrahydrofolic acid (or the growth factor of Leuconostoc citrovorum), belonging to the series of so-called "natural" configuration, the calcium salt of this acid being known as "Calcium Leucovorin"
5-CHO-(6R)-THF = 6R diastereoisomer of folinic acid, belonging to the series of so-called "unnatural" configuration
5-Me-(6RS)-THF = (6RS)-5-methyl-5,6,7,8-tetrahydrofolic acid
5-Me-(6S)-THF = (6S)-5-methyl-5,6,7,8-tetrahydrofolic acid, belonging to the series of so-called "natural" configuration
5-Me-(6R)-THF = (6R)-5-methyl-5,6,7,8-tetrahydrofolic acid, belonging to the series of so-called "unnatural" configuration
[5,10-CH+-(6RS)-THF]X− = salt of (6RS)-$N^5,N^{10}$-methenyl-5,6,7,8-tetrahydrahydrofolic acid (or "anhydroLeucovorin") with the anion X−
[5,10-CH+-(6R)-THF]X− = salt of (6R)-$N^5,N^{10}$-methenyl-5,6,7,8-tetrahydrofolic acid with the anion X−, belonging to the series of so-called "natural" configuration
[5,10-CH+-(6S)-THF]X− = salt of (6S)-$N^5,N^{10}$-methenyl-5,6,7,8-tetrahydrofolic acid with the anion X−, belonging to the series of so-called "unnatural" configuration
[5,10-CH+-(6RS)-THF]X−.HX = salt of (6RS)-$N^5,N^{10}$-methenyl-5,6,7,8-tetrahydrofolic acid with the anion X− and the acid HX
[5,10-CH+-(6S)-THF]X−.HX = salt of (6S)-$N^5,N^{10}$-methenyl-5,6,7,8-tetrahydrofolic acid with the anion X− and the acid HX
5,10-CH$_2$-(6RS)-THF = (6RS)-$N^5,N^{10}$-methylene-5,6,7,8-tetrahydrofolic acid
5,10-CH$_2$-(6R)-THF = (6R)-$N^5,N^{10}$-methylene-5,6,7,8-tetrahydrofolic acid, belonging to the series of so-called "natural" configuration
5,10-CH$_2$-(6S)-THF = (6S)-$N^5,N^{10}$-methylene-5,6,7,8-tetrahydrofolic acid, belonging to the series of so-called "unnatural" configuration
b) the other abbreviations
DMSO = dimethyl sulfoxide
FAB = fast atomic bombardment
HPLC = high performance liquid chromatography
H-TSA = p-toluenesulfonic acid
MS = mass spectrometry
MS(FAB) = mass spectrometry with fast atomic bombardment device
Py = pyridine
RT = room temperature (15°–20° C.)
TSA− = p-toluenesulfonate ion

PRIOR ART

Commercial folinic acid [or 5-CHO-(6RS)-THF], which has the nomenclatures (6RS)-5-formyl-5,6,7,8-tetrahydrofolic acid and (6RS)-5-formyl-5,6,7,8-tetrahydropteroyl-L-glutamic acid and which is prepared in particular, with its calcium salt, from folic acid or from $N^5,N^{10}$-methenyl-5,6,7,8-tetrahydrofolic acid [see, for example, patent documents CH-A-496 012 and GB-A-1 560 372], is known to be a 1/1 molar mixture of two diastereoisomers which differ from one another by their configuration at $C^6$ (the carbon atom in the 6 position of the pteridinyl ring).

It is known that patent document GB-A-1 560 372 envisages in its description (see page 2, lines 4–6) the use of a complex - internal salt or zwitterion - of anhydro-Leucovorin (the compound of the formula [5,10-CH+-(6RS)-THF]X−) in which one of the carboxylate ions, COO−, of the R-p-benzoyl-(L)-glutamic acid residue has reacted with the positive charge delocalized over the $N^5$, $C^{11}$ and $N^{10}$ atoms, as a starting material in the synthesis of (6RS)-folinic acid and its calcium salt.

It is known from the article by J. C. FONTECILLA-CAMPS et al., J. Am. Chem. Soc., 101, 6114 (1979), that the biologically active diastereoisomer of folinic acid has the 6S configuration. It is pointed out that this diastereoisomer has in the past been called on the one hand the "natural isomer" by way of convenience because of its biological activity, and on the other hand "(1,L)-folinic acid", where the term "1" refers to the configuration at $C^6$ and the term "L" refers to the configuration of the glutamic acid side-chain.

(6RS)-Folinic acid, 5-CHO-(6RS)-THF, is generally and commonly used, with its calcium salt, as a therapeutic means of "relief" in patients undergoing anticancer chemotherapy based on methotrexate, and as a means of increasing the inhibition of thymidylate synthetase by anticancer agents such as 5-fluorouracil and 5-fluoro-2'-deoxyuridine.

The 6R diastereoisomer of folinic acid, called the "unnatural isomer" (as opposed to the biologically active 6S) by way of convenience, was long thought to be inactive; however, it has been indicated [see F. M. SIROTNAK et al., Biochem. Pharm., 28, 2993 (1979), and J. K. SATO et al., Proc. Am. Assoc. Cancer Res., 25, 312 (1984)] that said 6R diastereoisomer is capable of interfering with the transport or the polyglutamation of the active 6S diastereoisomer.

As far as folinic acid is concerned, there is consequently a need to develop a technique of obtaining the pure 6S diastereoisomer by separation of the (6RS) mixture or by stereospecific synthesis.

The techniques described by D. B. COSULICH et al., J. Am. Chem. Soc., 74, 4215 (1952) [proposing the separation of the stereoisomers of folinic acid by fractional crystallization of their calcium salts in water], on the one hand, and by C. TEMPLE et al., Cancer Treatment Reports, 65, 1117 (1981) [proposing the separation of (6S)-folinic acid from the (6RS) mixture by differential solubilization of the calcium salts in water], on the other, happen to be ineffective since they produce a mixture of 6S and 6R in a molar ratio of 1/1.

To isolate calcium (6S)-folinate from the (6RS) mixture, published PCT international patent application WO-A-8808844 (EPROVA) has recommended another method, which is based on the preferential crystallization of calcium (6S)-folinate from an aqueous alkaline medium containing excess $Ca^{2+}$.

It is further known that other reduced folates have been obtained in a diastereoisomerically pure form, either from (6S)- and (6R)-tetrahydrofolic acids prepared by an enzymic method [see especially F. M. SIROTNAK et al., Biochem Pharm., 28, 2993 (1979) cited above, H. C. S. WOOD et al., Chem. and Biol. of Pteridines, 533 (1983), and P. L. CHELLO et al., Biochem. Pharm., 31, 1527 (1982)], or else by other lengthy and tedious chemical and chromatographic methods [see especially B. T. KAUFMAN et al., J. Biol. Chem., 238, 1498 (1963), S. B. HORWITZ et al., J. Med. Chem., 49 (1969), B. V. RAMASASTRY et al., J. Biochem. Biophys. Res. Comm., 12, 478 (1963), J. C. WHITE et al., Chem. and Biol. of Pteridines, 625 (1979), and J. FEENEY et al., Biochemistry, 20, 1837 (1981)]; now, it so happens that all these methods, producing very small amounts (of the order of a milligram) of products which have not been isolated in the form of crystalline solids or which have been obtained in the form of lyophilized powder whose purity is always less than or equal to 80%, are unsatisfactory.

Furthermore, it so happens that attempts to reduce dihydrofolic acid asymmetrically by a chemical method have never met with success [see L. REES et al., Tetrahedron, 42, 117 (1986)].

The availability of large amounts of diastereoisomerically pure reduced folates would make it possible clearly to compare and assess the enzymic, biological and/or therapeutic activities of each diastereoisomer. In fact, the majority of experiments undertaken hitherto have been conducted either with a 1/1 molar mixture of the diastereoisomers or with the so-called "natural" diastereoisomer, the activities of the so-called "unnatural" diastereoisomer being extrapolated from the values obtained for said 1/1 molar mixture and for said natural diastereoisomer [see especially J. A. STRAW et al., Cancer Research, 41, 3936 (1981)]. To the knowledge of the Applicants, the only "unnatural" folinic acid isomers with which experiments have been carried out are those of folinic acid and $N^5$-methyl-5,6,7,8-tetrahydrofolic acid, which have been obtained in situ by enzymic depletion (i.e. elimination or inhibition) of the corresponding "natural" isomer [see especially J. K. SATO cited above].

Finally, patent document EP-A-0 348 64; (publication date: Jan. 3, 1990) has disclosed two methods (I and II) of obtaining reduced folates having the configuration of the so-called "natural" series. According to method I, the complex salt called "(6RS)-5,10-methenyl-5,6,7,8-tetrahydrofolic acid chloride hydrochloride dihydrate", of the abbreviated formula [5,10-CH$^+$-(6RS)-THF]Cl$^-$.HCl.2H$_2$O, is treated with an HCOOH/2 N HCl mixture to give, by crystallization, the natural diastereoisomer of the formula [5,10-CH$^+$-(6R)-THF]Cl$^-$.HCl.

Method II comprises the following steps: firstly (according to Example 5.1 of patent document EP-A-0 348 641), (a) said afore-mentioned complex salt, of the formula [5,10-CH$^+$-(6RS)-THF]Cl$^-$.HCl.2H$_2$O, is solubilized in the acid HCOOH, (b) the resulting solution is treated with an anion exchange resin [AMBERLITE ® IRA-68], (c) the eluate which has been collected is evaporated under reduced pressure, and then (d) the resulting evaporation residue is treated with AcOH and MeOH to precipitate a product known as the internal salt of the acid 5,10-CH-(6RS)-THF; secondly (according to Example 11 of patent document EP-A-0 348 641), said internal salt is reacted with an aqueous solution of HCOOH at 20° C., with stirring, a precipitate is formed and the internal salt of the acid 5,10-CH-(6S)-THF, containing 73% of the diastereoisomer of 6S form, is collected by filtration (the proportion of the diastereoisomer of 6S form is increased to 90% by repeating the precipitation operation); treatment of the combined filtrates with acetone precipitates the internal salt of the acid 5,10-CH-(6R)-THF with a purity of 75%.

AIM OF THE INVENTION

According to the invention, a novel technical solution is proposed which makes it possible to synthesize the 6R and 6S diastereoisomers of reduced folates in order to meet the aforementioned needs. This novel technical solution differs from method II of patent document EP-A-0 348 641, referred to above, especially in that the treatment with the anion exchange resin and then the AcOH/MeOH mixture is replaced with the reaction of 5-CHO-(6RS)-THF or [5,10-CH$^+$-(6RS)-THF]X$^-$ with the acid HCOOH at a pH within the range from 2.0 to 2.6.

This novel technical solution provides diastereoisomerically pure compounds, defined below, of 6P and 6Q configuration which very probably have formulae III and respectively IV given below. This technical solution constitutes a novel means of obtaining reduced folates since it makes it possible especially to prepare diastereoisomerically pure compounds, such as (6S)- and (6R)-folinic, (6S)- and (6R)-$N^5$,$N^{10}$-methylene-5,6,7,8-tetrahydrofolic and (6S)- and (6R)-$N^5$-methyl-5,6,7,8-tetrahydrofolic acids and their salts, from said diastereoisomers of formulae III and IV.

SUBJECT OF THE INVENTION

According to one feature of the invention, a method of preparing a compound derived from tetrahydrofolic acid, and its diastereoisomers, is recommended, said method comprising:

1) the reaction of a tetrahydrofolic acid compound selected from the group consisting of (i) the (6RS)-5-formyl-5,6,7,8-tetrahydrofolic acid of the formula

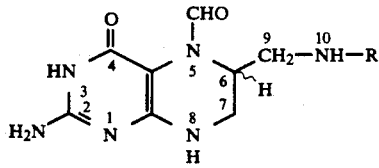

(I)

in which R is the p-benzoyl-(L)-glutamic acid residue of the formula

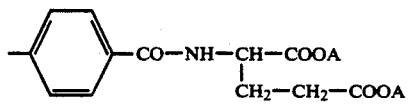

(XIII)

where A is H, and its salts, and (ii) the $N^5,N^{10}$-methenyl-5,6,7,8-tetrahydrofolic acid of the formula

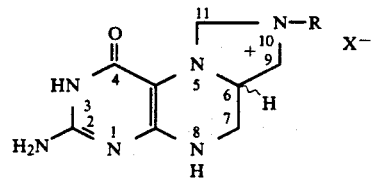

(II)

in which $X^-$ is an anion and R is as defined above, with HCOOH at a pH within the range from 2.0 to 2.6;

2) on the one hand the recovery of the precipitate which has formed, by filtration, and on the other hand the recovery of the corresponding filtrate;

3) the separation, from said precipitate, of a first pure diastereoisomer belonging to the series of unnatural configuration, hereafter called the 6Q diastereoisomer, and very probably having formula IV, by fractional recrystallization; and 4) if necessary, the separation, from said filtrate obtained according to step 2) and/or from the filtrates of recrystallization according to step 3), of a second pure diastereoisomer belonging to the series of natural configuration, hereafter called the 6P diastereoisomer, and very probably having formula III.

According to this method, a precipitate of the 6Q and 6P diastereoisomers in a molar ratio 6Q/6P of about 7/3 is obtained in step 2).

In formula II, the dotted bond—joining the $N^5$ and $N^{10}$ nitrogen atoms is intended to indicate that the positive charge is delocalized over the $N^5$, $C^{11}$ and $N^{10}$ atoms.

According to another feature of the invention, said 6Q and 6P diastereoisomers and mixtures thereof, especially the aforementioned 7/3 molar mixture, are proposed as novel industrial products. The 6P diastereoisomer belongs to the so-called natural series inasmuch as it leads to the diastereoisomers of reduced folates such as 5-CHO-(6S)-THF, 5,10-CH-(6R)-THF, 5,10-CH$_2$-(6R)-THF and 5-Me-(6S)-THF, and to their salts. The 6Q diastereoisomer belongs to the so-called unnatural series inasmuch as it leads to the diastereoisomers of reduced folates such as 5-CHO-(6R)-THF, 5,10-CH-(6S)-THF, 5,10-CH$_2$-(6S)-THF and 5-Me-(6R)-THF, and to their salts.

According to yet another feature of the invention, it is recommended to use said 6P and 6Q diastereoisomers in order to obtain the diastereoisomerically pure reduced folates of the natural and unnatural series.

DETAILED DESCRIPTION OF THE INVENTION

The diastereoisomers according to the invention have been designated 6P and 6Q for the sake of convenience, because it was not possible to determine their configuration directly. Nevertheless, there are serious grounds for assuming that the 6P compound has the 6R configuration and that the 6Q compound has the 6S configuration; there are also serious grounds for considering that these diastereoisomers are compounds of the orthoamide type and have formulae III and IV (even though, in the current state of knowledge, these assumptions would be hypotheses which are not binding upon the Applicants).

As indicated above, the 6P diastereoisomer, belonging to the natural series, very probably has the formula

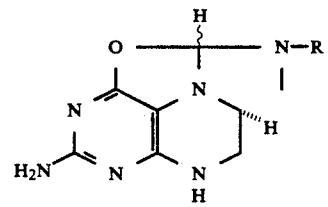

(III)

and the 6Q diastereoisomer very probably has the formula

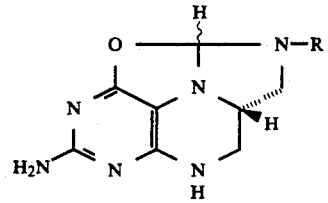

(IV)

The conversion of the 6P and 6Q orthoamide derivatives to 5-CHO-THF, 5-Me-THF and 5,10-CH$_2$-THF does not affect the stereochemistry of the $C^6$ center. Thus, on the one hand, the diastereoisomers belonging to the series of natural configuration have a spatial configuration at $C^6$ such as illustrated especially by formulae V, VII, VIII and XI below and, on the other hand, the diastereoisomers belonging to the series of unnatural configuration have a spatial configuration at $C^6$ such as illustrated especially by formulae VI, IX, X and XII below. By contrast, the R or S notation changes within each series in accordance with the rules of nomenclature; in the series of natural configuration, there is a change from the 6S diastereoisomer [for example 5-CHO-(6S)-THF or 5-Me-(6S)-THF] to the 6R diastereoisomer [for example 5,10-CH-(6R)-THF or 5,10-CH$_2$-(6R)-THF] when the bicyclic skeleton of the pteridinyl residue becomes tricyclic.

When carrying out step 1), it is important for the pH of the reaction medium to be adjusted to between 2.0 and 2.6. Adjustment of the pH within this range will advantageously be effected by the addition of NH$_3$ or NH$_4$OH. Preferably, in step 1), the pH of the reaction medium will be between 2.2 and 2.4 and more advantageously of the order of 2.30-2.35.

It will also be advantageous to carry out the reaction of step 1) for at least 0.25 h at a temperature of 40° to 65° C. and preferably at a temperature of 45°-60° C.

For practical reasons step 1) according to the invention will be carried out according to two different routes:

(a) II→III+IV
(b) I→III+IV

In route (a), the ammonia is incorporated directly into the mixture II +H₂O/HCOOH in order to regulate the pH, the reaction being carried out at a temperature of 55°-65° C. for at least 0.25 h. In route (b), compound I is reacted with an H₂O/HCOOH mixture at 60°-65° C. for at least 1 h, the resulting reaction medium is cooled to 40°-45° C. and the ammonia is then introduced, the reaction subsequently continuing at 40°-45° C. for at least 0.25 h.

In both routes, the reaction mixture gives, on cooling to RT, a bright yellow crystalline precipitate which is practically insoluble in the customary solvents.

The elemental analysis of this precipitate is in agreement with structures III and IV, said precipitate being a mixture of orthoamides resulting from (i) enolization of the exocyclic oxo group (in the C⁴ position of the pteridinyl skeleton) of the lactam group, and (ii) cyclization by the formation of a bond between the oxanion and the carbon atom at C¹¹ of formula II.

The orthoamide structure of the compounds of formulae III and IV is also confirmed by the following facts:

analysis of the compounds of formulae III and IV by mass spectrometry, MS(FAB), gives a practically identical spectrum to that of the precursor of formula II and indicates that the reaction II =III/IV represents a conversion of the protonation/deprotonation type; and a sample of the product III/IV, treated with excess p-toluenesulfonic acid, is indistinguishable from the product of formula II (or from the pair VII/IX) by HPLC analysis (on a non-chiral column).

According to the invention, the fractional crystallizations of steps 3) and 4) can be replaced with chromatography on a column for chiral separation. In practice, it is preferable to increase the proportions of diastereoisomers of natural configuration and unnatural configuration in compounds III and respectively IV by fractional crystallization and then, if necessary, to purify each product by HPLC on a chiral column.

To carry out the method of the invention, the anion X⁻ of the compound of formula II will be an appropriate anion and may be selected in particular from the group consisting of F⁻, Cl⁻, Br⁻, I⁻, NO₃⁻, ½SO₄²⁻, ⅓PO₄³⁻, oxalate, p-toluenesulfonate, maleate, benzenesulfonate, methanesulfonate, trifluoroacetate and trichloroacetate ions.

The orthoamides of formulae III and IV can be converted to compounds V and respectively VI by hydrolysis at 100° C. and at pH 7, and to their salts:

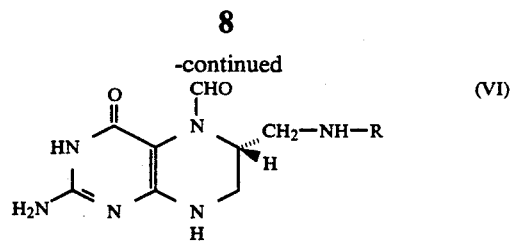

and

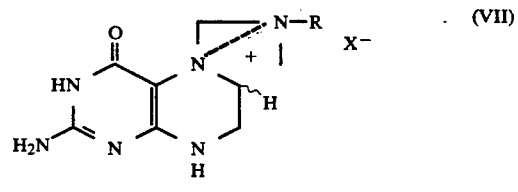

The orthoamides of formulae III and IV can also be used to prepare the diastereoisomerically pure acids 5,10-CH₂-(6R)-THF of formula VIII and respectively 5,10-CH₂-(6S)-THF of formula X, and their salts, by conversion of III and IV to VII and respectively IX, subsequent treatment with NaBH₄ in an aprotic solvent containing pyridine, and then purification in accordance with the teaching of Swiss patent application no. 02 736/89 to the applicants.

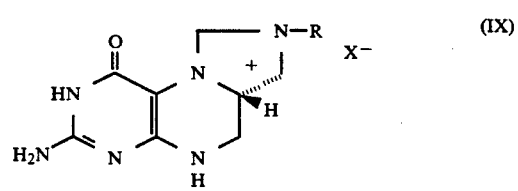

on the one hand, and

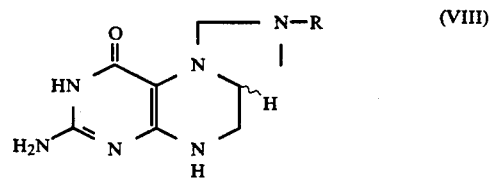

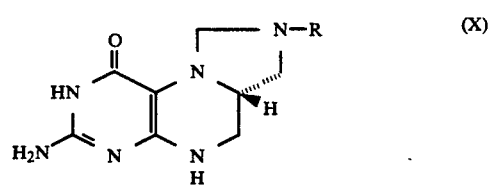

on the other.

In the synthesis of the compounds of formulae VIII and X (or of formulae XI and XII), intermediates VII and respectively IX can be isolated if necessary. However, such an operation is not essential and the remainder of the synthesis is generally carried out without isolating said compound VII or respectively IX.

Likewise, the orthoamides of formulae III and IV can be used to prepare the diastereoisomerically pure acids 5-Me-(6S)-THF of formula XI and respectively 5-Me-(6R)-THF of formula XII, and their salts, by conversion to VII and respectively IX and then reduction with NaBH₃CN in an aprotic solvent:

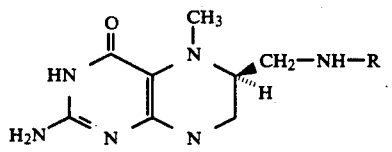

and

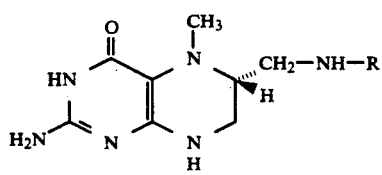

The salts of the diastereoisomers of natural configuration of formulae V, VIII and XI, on the one hand, and those of unnatural configuration of formulae VI, X and XII, on the other, include, according to the invention, (i) the metal salts, especially those of alkali and alkaline earth metals such as Na, K, Ca and Mg, and (ii) the addition salts obtained with organic bases such as, in particular, ethylamine, 2-(N,N-dimethylamino)ethanol, 2-(N,N-diethylamino)ethanol, morpholine, piperidine and the like.

The best mode of carrying out the invention is illustrated by the following reaction schemes:

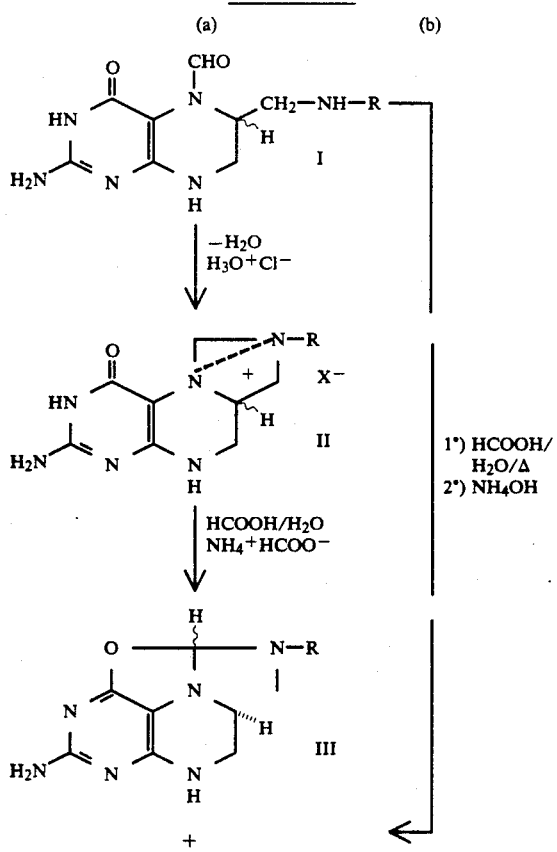

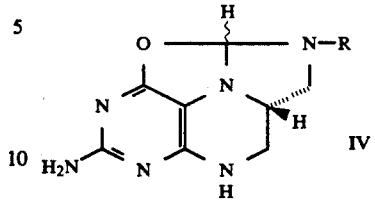

where the group A present in the residue R of formula I is ½Ca$^{2+}$, the group A present in the residue R of formulae II, III and IV is H and the group X$^-$ present in formula II is Cl$^-$.

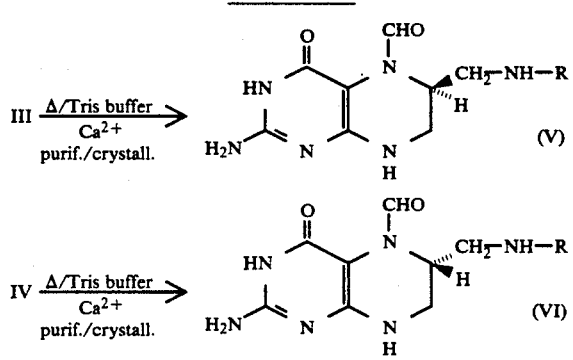

where the group A present in the residue R of formulae V and VI is ½Ca$^{2+}$ and the group A present in the residue R of formulae III and IV is H.

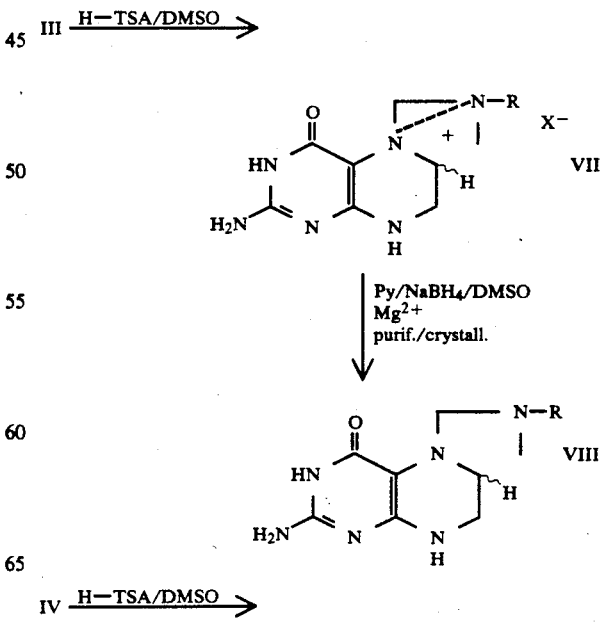

-continued
SCHEME 3

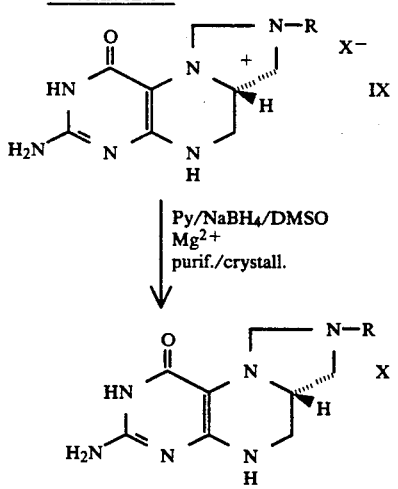

where the group A present in the residue R of formulae VIII and X is ½ $Mg^{2+}$, the group A present in the residue R of formulae III, IV, VII and IX is H and the group $X^-$ present in formulae VII and IX is the p-toluenesulfonate ion ($TSA^-$).

SCHEME 4

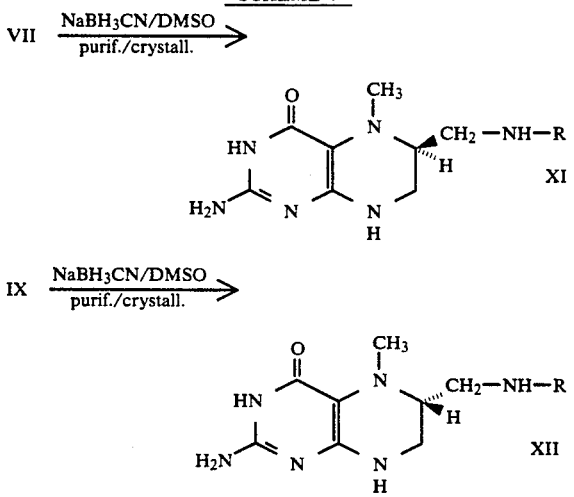

where the group A present in the residue R of formulae VII, IX, XI and XII is H and the group $X^-$ present in formulae VII and IX is the p-toluenesulfonate ion.

Further advantages and characteristics of the invention will be understood more clearly from the following description of Preparatory Examples, which in no way imply a limitation but are given by way of illustration.

PREPARATION I

Preparation of the orthoamide of formula III (Example 1) and the orthoamide of formula IV (Example 2)

Aqueous ammonia is added to a mixture of 1200 ml of water and 270 ml of formic acid, stirred at RT and under an inert atmosphere (nitrogen or argon), in a sufficient amount to bring the pH to 2.3. The resulting solution is heated to 60° C. and 15.41 g of [5,10-$CH^+$-(6RS)-THF]$X^-$ of formula II (where X=Cl, obtained by the method described by C. TEMPLE et al., J. Med. Chem., 22, 731 (1979)) are added. Stirring is maintained until the solids have totally dissolved. The reaction medium is filtered and the filtrate is left to stand at RT for 48 h. The bright yellow bulky precipitate which has formed is collected by filtration on a Büchner funnel, washed with water and then acetonitrile (the filtrates are collected for subsequent treatment) and dried for 1 h under reduced pressure at 50° C. to give 7.76 g (yield: 54%) of a mixture of the orthoamides of formulae III and IV.

To determine the molar ratio of the two diastereoisomers, a sample of the mixture thus obtained is converted to a mixture of $N^5$-methyltetrahydrofolic acids of formulae XI and XII and then analyzed by HPLC using a RESOLVOSIL® chiral column in accordance with the teaching of K. E. CHOI et al., Anal. Bioch., 168, pages 398–404 (1988). For this purpose, 11 mg of the mixture III/IV which has been obtained are suspended in 1.5 ml of an aqueous solution of p-toluenesulfonic acid containing 18 g/l; a solution of 6 mg of $NaBH_3CN$ in a small amount of water is added and the resulting mixture is stirred for 0.25 h at RT; this mixture is diluted with 7.5 volumes of water before being introduced into the HPLC system. It is deduced (from the ratio of the diastereoisomers XII/XI) that, in said mixture III/IV, the two diastereoisomers are in a molar ratio IV/III of 7/3.

Repeated recrystallization of said mixture III/IV from $H_2O$/HCOOH (6/1 v/v) gives 1.1 g (yield: 15.4%) of the diastereoisomerically pure orthoamide of formula IV.

The mother liquors from the preparation of compound IV are combined, treated with 190 ml of water and left to stand at 4° C. for 62 h. This gives a bright yellow precipitate, which is isolated by filtration, washed with $H_2O$ and then acetonitrile and dried under reduced pressure for 1 h at 50° C. to give 2.2 g of a product which consists (according to HPLC analysis on a RESOLVOSIL® column) of a mixture III/IV in a molar ratio of 96/4. This mixture is recrystallized as follows: $NH_4OH$ is added to a mixture of 252 ml of water and 57 ml of HCOOH, stirred at RT and under an inert atmosphere, in a sufficient amount to adjust the pH to 2.3; the resulting mixture is heated to a temperature of 60° C. and said mixture III/IV (96/4) is then added; stirring is continued until dissolution is complete; the resulting reaction medium is then filtered hot on a Büchner funnel and the filtrate is left to stand at RT for 8 h and then at 4° C. for 60 h; the bright yellow solid which has precipitated is isolated by filtration, washed with water and then acetonitrile and dried under reduced pressure for 1 h at 50° C. to give 1.41 g (yield: 20%) of the diastereoisomerically pure orthoamide of formula III, as confirmed by analysis on a RESOLVOSIL® column.

PREPARATION II

Preparation of the orthoamide of formula III (Example 1) and the orthoamide of formula IV (Example 2) from the calcium salt of (6RS)-folinic acid 18.9 g of calcium folinate pentahydrate of formula I are added to a mixture of 464 ml of water and 136 ml of HCOOH, stirred at 55°–60° C. and under an inert atmosphere in a reactor provided with a pH electrode, and the resulting mixture is stirred at 55°–60° C. for 1 h. Said mixture is cooled to 45° C., the pH (apparent) is adjusted to 2.35 by dropwise addition of the appropriate amount of concentrated aqueous ammonia, and the mixture is stirred overnight at RT. The yellow precipitate which has formed is isolated by filtration and washing with water and then acetone. Drying under reduced pressure at 50° C. for 1 h gives 8.81 g of a mixture IV-/III in a molar ratio of 7/3 according to the aforementioned analysis on a RESOLVOSIL ® column.

Repeated recrystallization of this mixture from $H_2O$/HCOOH (6/1) gives 1.32 g (yield: 18.4%) of the diastereoisomerically pure orthoamide of formula IV (confirmation by HPLC analysis as indicated above). Elemental analysis for $C_{20}H_{22}N_7O_6.4H_2O$: theory: C=45.55%; H=5.54%; N=18.59%, found: C=45.91%; H=5.27%; N=18.45%, Mass spectrum by MS(FAB) (matrix: thioglycerol; 8 keV): 456($m^+$, 100), 412(7.5), 410(9.1), 326(10), 311(7.0), 283(11.6), 282(21.2).

The mother liquors are combined and diluted with 80 ml of water. The mixture is cooled to 0° C. and stirred at this temperature under an inert atmosphere for 24 h. The precipitate formed is collected by filtration on a Büchner funnel, washed with water and then acetone and dried under reduced pressure at 50° C. to give 2.67 g of a product which consists of III/IV in a molar ratio of 98/2 according to the afore-mentioned HPLC analysis on a RESOLVOSIL ® column. By recrystallization according to the procedure given in Preparation I above (for obtaining compound III), 1.91 g (yield: 23.9%) of the diastereoisomerically pure product of formula III are collected (confirmation by afore-mentioned HPLC on a RESOLVOSIL ® column).

Elemental analysis for $C_{20}H_{21}N_7O_6.HCOOH.\frac{1}{2}H_2O$ theory: C=49.42%; H=4.74%; N=19.21%, found: C=49.45%; H=4.70%; N=19.45%.

Mass spectrum by MS(FAB) (matrix: thioglycerol; 8 keV): 456($m^+$, 100), 412(13.3), 410(10.8), 326(13.3), 311(10.4), 283(13.7), 282(24.1), 232(39.4).

PREPARATION III

Preparation of the calcium salt of 5-CHO-(6S)-THF (Example 3; formula V)

80 g of the pure diastereoisomer III obtained according to Preparation II above, and then 100 ml of a 2M aqueous solution of tris(hydroxymethylamino)methane, are added to a degassed mixture of 2 liters of water and 20 ml of 2-mercaptoethanol, stirred at RT under an inert atmosphere in a reactor provided with a reflux condenser and a pH electrode. The resulting mixture is heated to 45°–50° C. and the pH is kept at 7.3 by addition of the necessary amount of the tris-(hydroxymethylamino)methane solution until the solid has completely dissolved. The resulting medium is refluxed for 4.5 h; 3.3 g of carbon black are added to the hot solution and stirring is continued for 1 h while said medium is being cooled to RT. After filtration of the reaction medium on Célite, 87 ml of a 2M aqueous solution of $CaCl_2$ are added to the filtrate and the resulting solution is diluted slowly with 3.6 liters of EtOH (94%). Said solution diluted in this way is kept overnight at 0° C. and the precipitate formed is collected by filtration and washed with EtOH (94%) and then MeCOMe. Drying under reduced pressure at 50° C. for 2 h gives 79 g of crude calcium (6S)-folinate. This product has an HPLC purity of 96%; repeated recrystallization from $H_2O$ and drying under reduced pressure at 50° C. gives 43.5 g (yield: 48.5%) of pure calcium (6S)-folinate.

Analyses $H_2O$ content (according to FISCHER): 15%
Ca content: 8.11% (theory: 7.84%)
HPLC purity: 100%
HPLC test [against the (6RS) standard of the US Pharmacopeia]: 99.5%
diastereoisomeric purity (evaluated on a chiral column): 100%
UV spectrum (20 mg/l in 0.01N NaOH):
 $\lambda_{max}$=282 nm ($\epsilon$=30,060)
 $\lambda_{min}$=242 nm
 ratio of the 2 absorption peaks $A_1/A_2$=4.96
$[\alpha]_D$= −14.6° (c=1 in $H_2O$)

PREPARATION IV

Preparation of the calcium salt of 5-CHO-(6R)-THF (Example 4; formula VI)

The expected product is obtained by following the procedures described in Preparation III above, except that the diastereoisomer of formula III is replaced with the diastereoisomer of formula IV.

Analyses $H_2O$ content (according to FISCHER): 10.2%
HPLC purity: 99%
HPLC test [against the (6RS) standard of the US Pharmacopeia]: 95%
diastereoisomeric purity (evaluated on a chiral column): greater than 98%
UV spectrum (20 mg/l in 0.01N NaOH):
 $\lambda_{max}$=282 nm ($\epsilon$=28,350)
 $\lambda_{min}$=242 nm
 ratio of the 2 absorption peaks $A_1/A_2$=4.25
$[\alpha]_D$= +39.8° (c=1 in $H_2O$)

PREPARATION V

Preparation of the magnesium salt of 5,10-$CH_2$-(6S)-THF (Example 5; formula X)

10 g of the orthoamide diastereoisomer of formula IV are suspended in a solution of 4.18 g of H-TSA in 130 ml of dry DMSO and the suspension is stirred at RT under an inert atmosphere until dissolution is complete. 44 ml of pyridine are added at RT and a solution of 880 mg of $NaBH_4$ in 44 ml of DMSO is then added slowly (over 10 minutes). After the resulting mixture has been stirred at RT for a period of 10 minutes, the reaction medium is cooled by means of an ice bath and diluted dropwise with one liter of methyl ethyl ketone. The mixture is stirred for 20 minutes at 0° C. and the yellow precipitate formed is collected by filtration; this precipitate is washed with acetone (twice) and dried under reduced pressure at 50° C. for 1 h to give 6.14 grams of crude 5,10-$CH_2$-(6S)-THF (probably in the form of a mixed $Na^+$/pyridinium salt). This product has an apparent HPLC purity of 87.2% and contains about 11% of 5-Me-THF.

This crude product is added in portions to 80 ml of water containing traces of NaOH, with stirring at 0° C. under an inert atmosphere: during this operation, the pH is kept at about 9.0 by the addition of 1N NaOH as required. 6.0 ml of a 2M aqueous solution of $MgCl_2$ are added to the resulting solution, bringing the pH to 8.4. The small amount of insoluble material is removed by filtration on Célite. The resulting filtrate is stirred at 0° C. while at the same time being diluted dropwise with 105 ml of acetone; after stirring for a further 45 minutes at 0° C., the precipitate is collected by filtration, washed (twice) with acetone and dried under reduced pressure at 50° C. for 1 h to give 3.9 g of the expected magnesium salt of formula X.

Analyses $H_2O$ content (according to FISCHER): 14%

HPLC purity: 92.3% (the product contains 6% of 5-Me-(6R)-THF)
diastereoisomeric purity (evaluated on a chiral column): greater than or equal to 98%
UV spectrum (20 mg/l in 0.01N NaOH):
$\lambda_{max}$ = 296 nm ($\epsilon$=b 28,300)
$\lambda_{min}$ = 244.5 nm
ratio of the 2 absorption peaks $A_1/A_2$ = 3.68
$[\alpha]_D$ = 88.7° (c=1 in $H_2O$)

PREPARATION VI

Preparation of the magnesium salt of 5,10-$CH_2$-(6R)-THF (Example 6; formula VIII)

This product is obtained by procedures analogous to those described in Preparation V, starting from the orthoamide diastereoisomer of formula III.

Analyses
$H_2O$ content (according to FISCHER): 14.0%
HPLC purity: 95.7% (the product contains 3.6% of 5-Me-(6S)-THF)
diastereoisomeric purity (evaluated on a chiral column): equal to 99%
UV spectrum (20 mg/l in 0.01N NaOH):
$\lambda_{max}$ = 296 nm ($\epsilon$=28,300)
$\lambda_{min}$ = 245 nm
ratio of the 2 absorption peaks $A_1/A_2$ = 4.11
$[\alpha]_D$ = +123.9° (c=1 in $H_2O$)

PREPARATION VII

Preparation of the acid 5-Me-(6S)-THF (Example 7; formula XI)

1.0 g of the orthoamide diastereoisomer of formula III is added to a solution of 910 mg of H-TSA in 53 ml of water, stirred at RT and under an inert atmosphere. A solution of 500 mg of sodium cyanoborohydride in 1 ml of water is subsequently added dropwise and the resulting mixture is then stirred for 5 h at RT; a white precipitate forms which is isolated by filtration, washed with cold water, ethanol and then acetone and dried under reduced pressure at 50° C. for 1 h to give 923 mg of the crude acid of formula XI.

This crude product is suspended in a mixture of 37 ml of water and 0.25 ml of 2-mercaptoethanol. The resulting mixture is stirred at RT under an inert atmosphere and 1N NaOH is added in a sufficient amount to produce complete dissolution. The solution is filtered and the filtrate is acidified by the dropwise addition of 1N HCl until the pH is 3.5. After the resulting suspension has been stirred for 1 h at 0° C., it is centrifuged and the solid is resuspended initially in water, then in ethanol and finally in acetone. After drying under reduced pressure at 50° C. for 1 h, 636 mg of the expected acid of formula XI are obtained.

Analyses
$H_2O$ content (according to FISCHER): 10%
HPLC purity: 96.0%
diastereoisomeric purity (evaluated on a chiral column): equal to 100%
UV spectrum (20 mg/l in 0.1M phosphate buffer; pH 6.5):
$\lambda_{max}$ = 290 nm ($\epsilon$=32,100)
$\lambda_{min}$ = 245 nm
ratio of the 2 absorption peaks $A_1/A_2$ = 3.65
$[\alpha]_D$ = +38.0° (c=0.5 in 0.1M phosphate buffer; pH 6.5)

PREPARATION VIII

Preparation of the acid 5-Me-(6R)-THF (Example 8; formula XII)

The expected acid of unnatural configuration is obtained by following the procedures described in Preparation VII, except that the diastereoisomer of formula III is replaced with the diastereoisomer of formula IV.

Analyses
$H_2O$ content (according to FISCHER): 11.5%
HPLC purity: 96.3%
diastereoisomeric purity (evaluated on a chiral column): equal to 100%
UV spectrum (20 mg/l in 0.1M phosphate buffer; pH 6.5):
$\lambda_{max}$ = 290 nm ($\epsilon$=32,500)
$\lambda_{min}$ = 245 nm
ratio of the 2 absorption peaks $A_1/A_2$ = 3.74
$[\alpha]_D$ = −9.2° (c=0.5 in 0.1M phosphate buffer; pH 6.5)

THERAPEUTIC USE $N^5,N^{10}$-Methylene-(6S)-5,6,7,8-tetrahydrofolic acid of formula X and its salts (especially the magnesium salt obtained by the method of Preparation V above) are diastereoisomerically pure products which belong to the series of the reduced folates of unnatural configuration and which are useful in therapeutics. It has been found that they inhibit thymidylate synthetase and are advantageously intended for cytostatic use in therapeutics, especially against cancer.

According to the invention, the diastereoisomerically pure acid 5,10-$CH_2$-(6S)-THF and its diastereoisomerically pure salts are therefore recommended as novel industrial products.

It is also recommended to use a diastereoisomerically pure substance, selected from the group consisting of the acid 5,10-$CH_2$-(6S)-THF, its non-toxic salts and mixtures thereof, in order to obtain a drug which inhibits thymidylate synthetase and which is intended for cytostatic use in therapeutics, especially against cancer.

As a variant, it is also recommended to use (1) said diastereoisomerically pure substance, selected from the group consisting of the acid 5,10-$CH_2$-(6S)-THF, its non-toxic salts and mixtures thereof, in association with (2) an antineoplastic agent selected in particular from 5-fluorouracil, 5-fluoro-2'-deoxyuridine, methotrexate, cis-platinum and mixtures thereof.

In this last use, said substance (1) and said agent (2) are advantageously presented in the form of a composition in association with a physiologically acceptable excipient. The association (1) + (2) offers the advantage of having synergistic effects.

Furthermore, it has just been found that the diastereoisomer 5-CHO-(6R)-THF of the series of so-called unnatural configuration, and its salts, possess cytostatic properties of interest in therapeutics. The fact that it has been possible to detect these cytostatic properties is (i) surprising inasmuch as 5-CHO-(6S)-THF of the series of so-called natural configuration, commercial folinic acid of the formula 5-CHO-(6RS)-THF and their salts have hitherto been used to limit the effects of cytostatic agents such as methotrexate, and (ii) beneficial inasmuch as 5-CHO-(6R)-THF and its salts, which have a low toxicity, can advantageously replace, totally or partially, the reference cytostatic or antineoplastic agents which are well known to be very toxic or detrimental towards the cell, such as methotrexate.

In the current state of knowledge, the Applicants assume that the cytostatic effect which has been detected for 5-CHO-(6R)-THF and its salts is due to a beneficial action of these products on one or more essential enzymes of cells; however, the Applicants are in no way bound by this theoretical aspect.

Thus, according to the invention, a novel use is recommended of a diastereoisomerically pure substance, selected from the group consisting of (6R)-5-formyl-5,6,7,8-tetrahydrofolic acid of the formula 5-CHO-(6R)-THF, its non-toxic salts and mixtures thereof, in order to obtain a cytostatic drug intended for use in therapeutics to combat neoplastic diseases, especially cancer.

Of course, according to the invention, within the scope of the novel use of 5,10-CH$_2$-(6S)-THF, 5-CHO-(6R)-THF and their non-toxic salts as cytostatic active principles, each active principle will be present at a therapeutically effective dose. To this end, the composition used will contain, in association with a physiologically acceptable excipient, a cytostatically effective amount of an active ingredient selected from (a) the compound 5,10-CH$_2$-(6S)-THF, its non-toxic salts and mixtures thereof, and (b) the compound 5-CHO-(6R)-THF, its non-toxic salts and mixtures thereof.

What is claimed is:

1. A method of preparing compounds of the formula

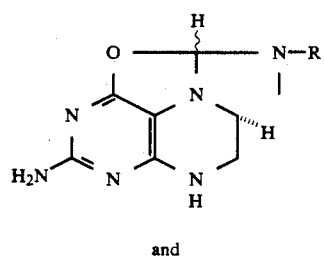

(III)

and

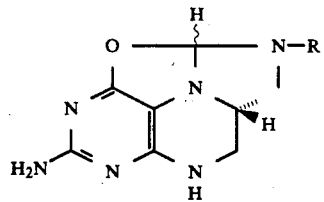

(IV)

said method comprising:
1) the reaction of a tetrahydrofolic acid compound selected from the group consisting of
   (i) the (6RS)-5-formyl-5,6,7,8-tetrahydrofolic acid of the formula

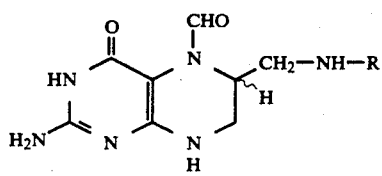

(I)

in which R is the p-benzoyl-(L)-glutamic acid residue of the formula

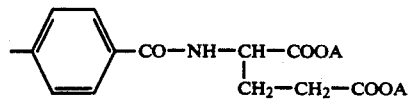

(XIII)

where A is H, and its salts, and
(ii) the N$^5$, N$^{10}$-methenyl-5,6,7,8-tetrahydrofolic acid compound of the formula

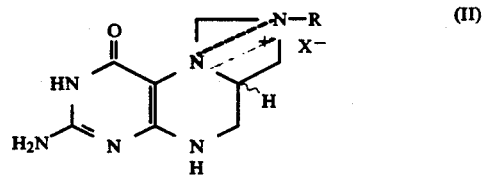

(II)

in which X$^-$ is an anion and R is as defined above, with HCOOH, said reaction comprising regulation of the pH within the range from 2.0 to 2.6;
2) on the one hand the recovery of the precipitate which has formed and on the other hand the recovery of the corresponding filtrate;
3) the separation, from said precipitate, of a first pure diastereoisomer belonging to the series of unnatural configuration; and
4) the separation, from said filtrate obtained according to step 2), of a second pure diastereoisomer belonging to the series of natural configuration.

2. A method according to claim 1 wherein step 1) comprises:
   (a) reacting the compound of formula I or one of its salts with an H$_2$O/HCOOH mixture for at least 1 h at a temperature of 55°–65° C.,
   (b) cooling the resulting mixture to 40°–45° C., and
   (c) continuing the reaction at 40°–45° C. for at least 0.25 h at a pH regulated to 2.0–2.6.

3. A method according to clam 2 wherein, in step 1), the pH of the reaction medium is adjusted to between 2.0 and 2.6 by the addition of aqueous ammonia.

4. A method according to claim 1 wherein step 1°) comprises:
   reacting the compound of formula II with an H$_2$O/HCOOH mixture for at least 0.25 h at a temperature of 55°–65° C. and at a pH regulated to 2.0–2.6.

5. A method according to claim 3 wherein, in step 1), the pH of the reaction medium is adjusted to between 2.0 and 2.6 by the addition of aqueous ammonia.

6. A method according to claim 1, wherein, in step 1), the pH of the reaction medium is adjusted to between 2.0 and 2.6 by the addition of aqueous ammonia.

7. A method according to claim 6 wherein, in step 1), the pH of the reaction medium is adjusted to between 2.2 and 2.4.

8. A method according to claim 1 wherein the separations of steps 3) and 4) comprise fractional crystallizations.

9. A method according to claim wherein the product obtained in step 2) is a mixture of III and IV in a molar ratio of about 7/3.

10. A tetrahydrofolic acid compound obtained by the method of step 4) of claim 1, which belongs to the series of natural configuration and has the following orthoamide formula:

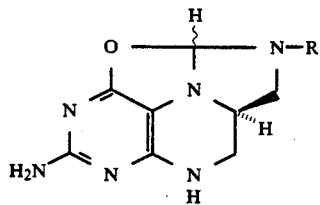
(III)
11. A tetrahydrofolic acid compound obtained by the method of step 3) of claim 1, which belongs to the series of unnatural configuration and has the following orthoamide formula:
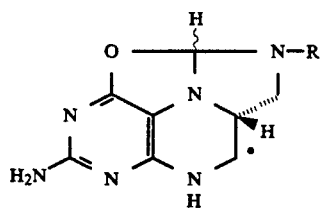
(IV)
* * * * *